United States Patent [19]
Krumeich et al.

[11] Patent Number: 5,108,412
[45] Date of Patent: Apr. 28, 1992

[54] SUCTION RING FOR SURGICAL OPERATIONS ON THE HUMAN EYE

[75] Inventors: Jorg H. Krumeich, Propst-Hellmich-Promenade 28, 4630 Bochum 6; Norbert Quast, Essen, both of Fed. Rep. of Germany

[73] Assignee: Jorg H. Krumeich, Fed. Rep. of Germany

[21] Appl. No.: 522,909

[22] Filed: May 14, 1990

[51] Int. Cl.$^5$ ............................................. A61M 35/00
[52] U.S. Cl. ................................. 606/166; 604/294; 623/4; 606/4; 606/107
[58] Field of Search .............. 604/294, 22, 300, 301; 606/4–6, 107, 166, 170; 623/4–6

[56] References Cited

U.S. PATENT DOCUMENTS

| | | | |
|---|---|---|---|
| 3,074,407 | 1/1963 | Moon et al. | 606/166 |
| 4,275,733 | 6/1981 | Marinoff | 606/107 |
| 4,619,259 | 10/1986 | Graybill et al. | 606/107 |
| 4,662,307 | 5/1987 | Hoffman et al. | 606/166 |
| 4,796,623 | 1/1989 | Krasner et al. | 604/22 |
| 5,011,498 | 4/1991 | Krumeich et al. | 606/166 |

FOREIGN PATENT DOCUMENTS

3909055A1  9/1990  Fed. Rep. of Germany .

*Primary Examiner*—C. Fred Rosenbaum
*Assistant Examiner*—Chalin Smith
*Attorney, Agent, or Firm*—Clifford A. Poff

[57] ABSTRACT

A suction ring apparatus for use in surgical eye operations comprising a right-angle section annular outer ring which retains an annular ring member of substantially triangular cross-section including an outer cylindrical wall surface, an annular end face surface and an eye-containing surface; the annular inner member has formed on its outer cylindrical wall surfaces and on the annular end face perpendicular thereto consecutive angularly spaced-apart discrete segments which engage an inner cylindrical wall surface and an annular inside end face surface of the outer ring and bound between the same and the inner member channels communicating with one another and with a vacuum bore associated with the outer ring which is connectable to a vacuum source; an edge of the outer ring defining a central aperture of the outer ring is dimensioned so that its diameter corresponds to the diameter of the corneal limbus and rests thereupon in operation. With such a construction, distortion of the eye is avoided and the apparatus can be non-movably disposed exactly in the limbus plane without contacting the cornea such that a trepan attached to the apparatus always moves within the optical axis.

7 Claims, 3 Drawing Sheets

SUCTION RING FOR SURGICAL OPERATIONS ON THE HUMAN EYE

BACKGROUND OF THE INVENTION

1. Field of the Invention

The present invention relates generally to surgical apparatus and, more particularly, to a suction ring apparatus which is fixable in position with respect to the human eye and which fixes the shape of the eye during surgical eye operations.

2. Description of the Prior Art

Rings of various constructions are used to stabilize the shape of the eye in eye operations. They can be sewn up, as in the case of Flieringa rings or they may be hollow rings whose cross-section is open towards the eye, of the kind used, for example, in refractive surgery (Barraquer rings). These latter rings are right-angled in cross-section, the open arms of the right angle engaging the eye and including between the same and the right-angle of the ring a space in which a negative pressure is produced. The negative pressure fixes the eye but increases the internal pressure therein. Rings of this kind cannot be used for eye operations in which the eye pressure must be maintained at normal pressures, i.e., in all eye-opening surgical techniques in which producing a negative pressure in the ring during the opening or cuttings of the eye would lead to the iris, lens and vitreous body advancing outwardly. These eye-opening operations are in particular those commonly practiced for cataract and perforating keratoplasties—i.e., the transfer of a corneal disc from a donor's eye to a patient's eye. An annular fixing of the eyeball which does not deform the eyeball and which does not increase pressure is desirable for all these eye-opening operations.

A suction ring comprising a right-angle section annular outer ring is described in pending U.S. patent application Ser. No. 462,052 filed Jan. 6, 1990 as a continuation of U.S. patent application Ser. No. 164,589, filed Mar. 7, 1988 and now abandoned, whose applicant is a joint inventor of the present invention. The annular outer ring of that application is formed with a bore which extends away from the ring axis and to which a hollow grip connectable to an external vacuum means can be connected; the outer ring carries an annular inner member which is engageable with the eye and which is substantially a right-angled triangle in cross-section.

It is an an object of the present invention to provide a suction ring apparatus for eye operations which enables the eye to be fixed reliably without deformation of the eyeball and without any increase in the internal pressure in the eye.

It is a further object of the present invention to provide a suction ring apparatus for eye operations which is non-movably disposed exactly in the limbus plane and does not contact the cornea.

It is a further object of the present invention to provide a suction ring apparatus for eye operations which ensures that a trepan (trephine) that is securable to the suction ring apparatus is always guided perpendicularly to the limbus plane and, therefore, always moves within the optical axis.

Still other objects and advantages will become apparent in light of the attached drawings and written description of the invention presented hereinbelow.

SUMMARY OF THE INVENTION

The present invention includes a right-angle section annular outer ring formed with a bore which extends away from the ring axis and to which a hollow grip connectable to an external vacuum means can be connected; the outer ring carries an annular inner member which is engageable with the eye and which is substantially a right-angled triangle in cross-section.

Further according to the present invention, the annular inner member carries both on its generated circumferential wall surface and on its end face perpendicular thereto consecutive angularly spaced-apart discrete segments which engage the inner cylindrical wall surface and the annular inside end face surface of the annular outer ring and bound between the same and the inner member channels communicating with one another and with the vacuum bore extending away from the ring axis, the annular inner member being connected to the annular outer ring by securing means which extend therethrough.

According to another feature of the invention, the securing means are releasable and extend through the annular outer ring end face.

Also according to the invention, the hand grip is releasaby secured to the annular outer ring.

The apparatus to the present invention is a suction ring which is placed on the eye concentrically of the cornea and is exhausted by an external exhauster or vacuum by way of a hollow grip communicating with the eye. The suction ring is made of components of steel or strong plastics. To obviate any increase in eye pressure the hollow section member, i.e., the outer ring portion of the suction ring, is covered towards the eye by an inner member substantially corresponding to the radius of the eye. Since the annular inner member of the present invention prevents deformation of the eye wall, eye pressure does not vary.

The annular inner member engages the inner cylindrical wall surface and the circular inner end face surface of the annular outer ring by way of discrete segments. The inner member is secured to the outer ring by pins or preferably, screwed fasteners which extend through the outer ring end face to engage in the discrete segments.

A fixing ring thus devised enables the surgeon to "mark out" or open the eye, it being possible for the knife to be guided along the inner boundary defining the inner aperture of the ring. This inner aperture can be reduced by the inclusion of concentric discs,if desired, which can be rotatably mounted and formed with recesses to receive a knife. The abutment edge for the knife can be devised in any desired manner so that the knife can be guided at any desired angle.

Another possibility is for the inner aperture to be so devised that it can be used to receive the base of a circular cutting knife, such as, for example, by means of a dovetail guide.

A special advantage of the suction ring according to the present invention is that it can be placed on the eye in the plane of the corneal limbus, i.e., the edge where the cornea of the eyeball merges into the sclera. To this end, according to the invention, the edge of the suction ring that limits the upper opening or aperture size of the ring is so dimensioned that its diameter corresponds to the diameter of the corneal limbus. The advantage of the ring being positioned accurately at this place is the certainty that the ring is non-movably disposed exactly in the limbus plane and does not contact the cornea. The securing of the ring to the limbus ensures that a trepan (trephine) which can be secured to the ring is always guided perpendicularly to the limbus plane and therefore always moves within the optical axis. Also, this type of ring fixing enables operations to be performed on the cornea without the cornea being deformed by the ring secured thereto and without the cornea being deformed while an incision is being made.

DESCRIPTION OF THE PREFERRED EMBODIMENT

Figure 1:
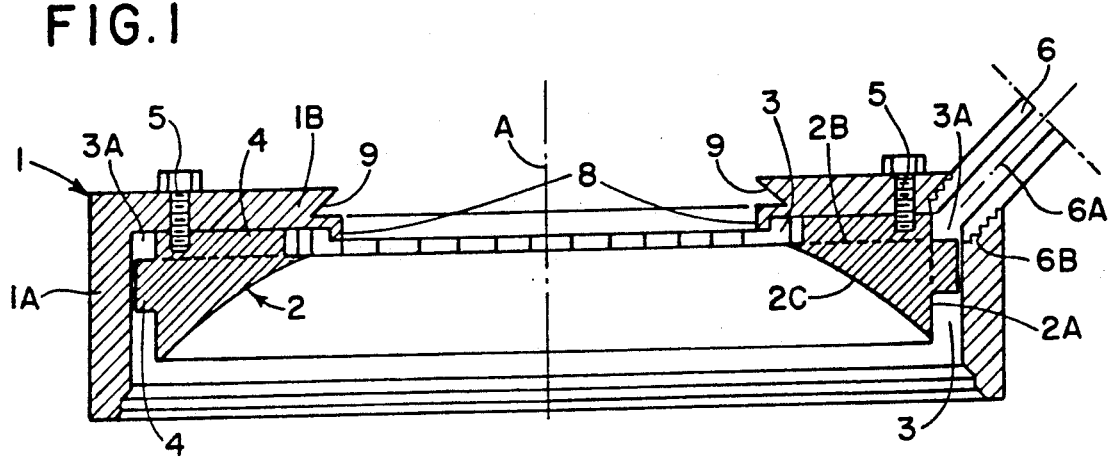
FIG. 1 is a section in front elevation of the suction ring apparatus of the present invention.
Figure 2:
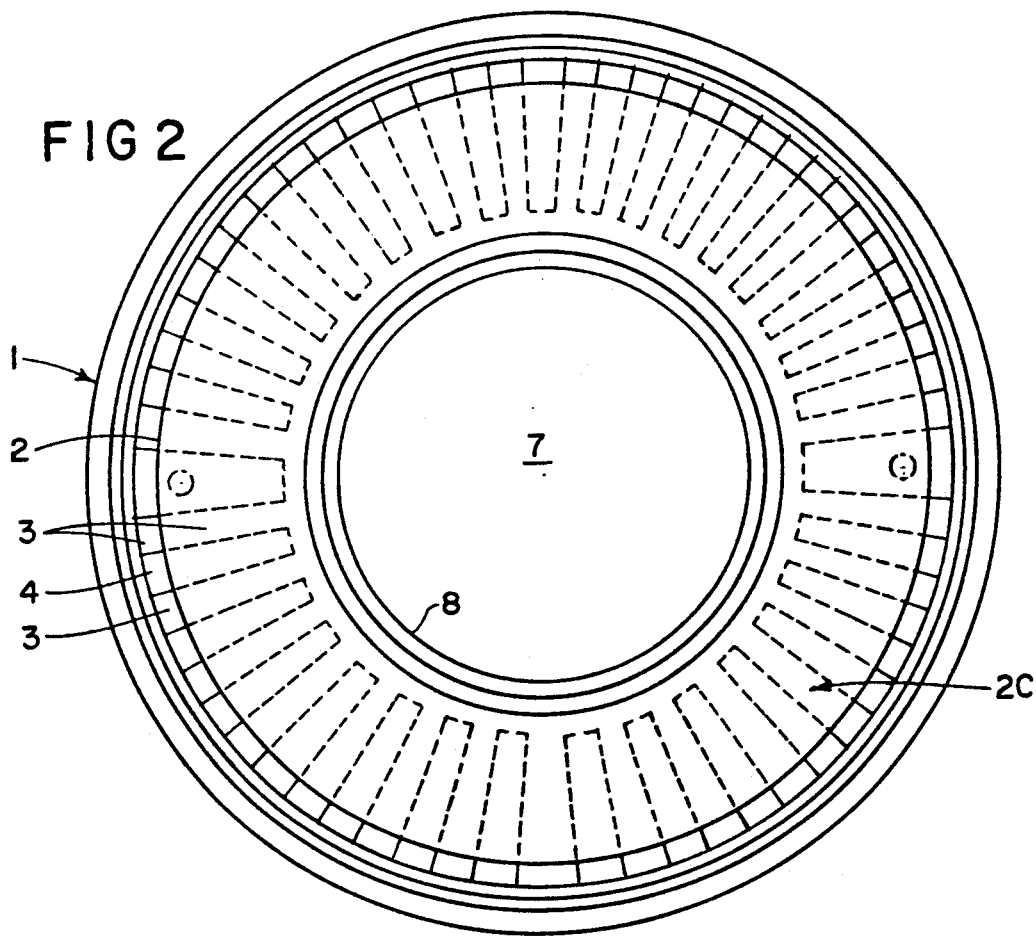
FIG. 2 is a bottom view looking into the suction ring apparatus of the present invention.
Figure 3:
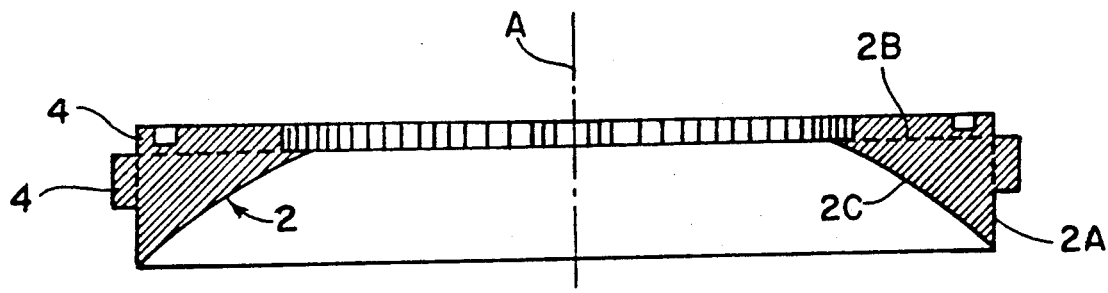
FIG. 3 is a view in section showing only the annular inner member of the section ring apparatus of the present invention.
Figure 4:
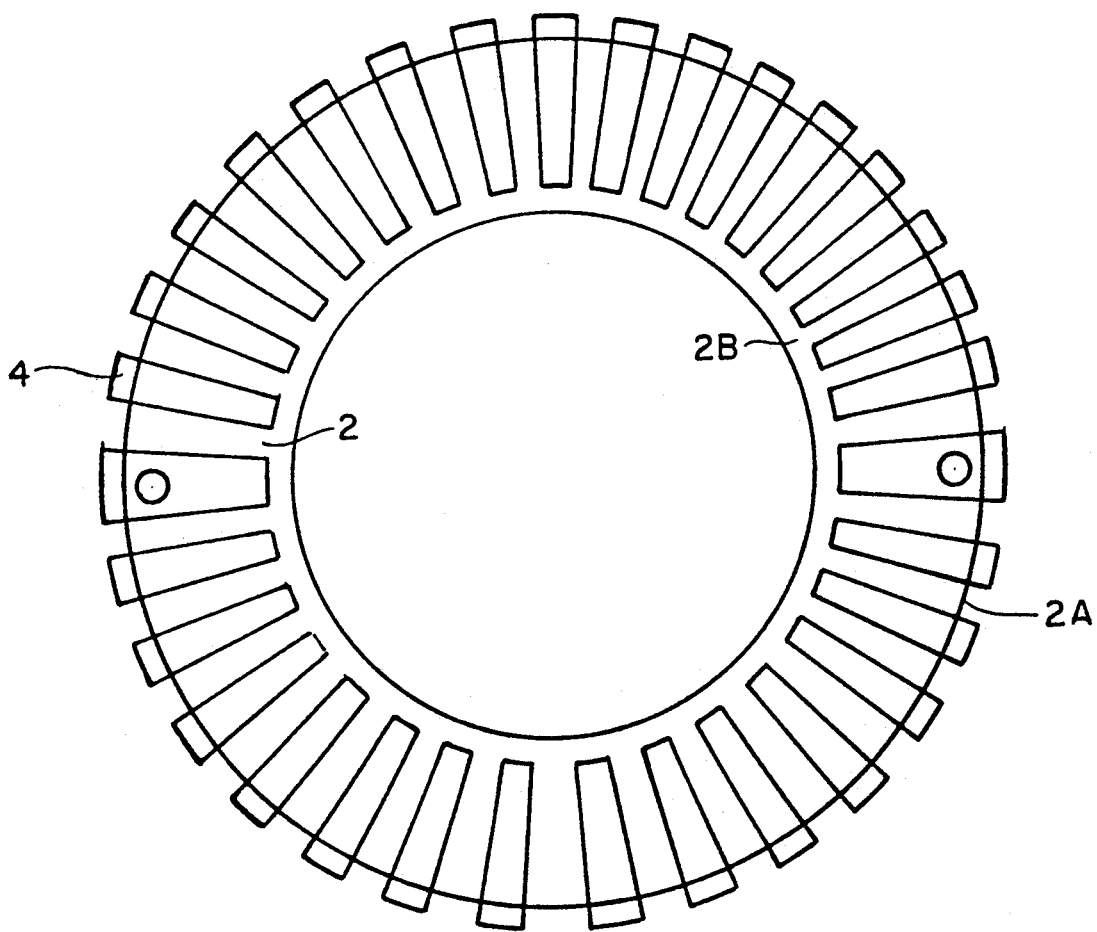
FIG. 4 is a plan view of the annular inner member depicted in FIG. 3.
Figure 5:
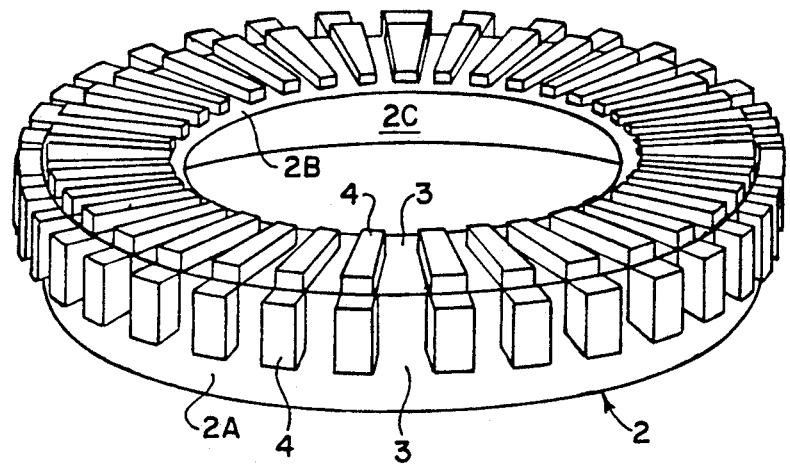
FIG. 5 is a perspective view of the annular inner ring member.

FIG. 1 is a view in cross-section of a preferably metal suction ring apparatus for surgical operations on the human eye constructed in accordance with the present invention. An annular outer ring portion 1 of the apparatus includes a cylindrical circumferential wall 1A and an end face 1B. The outer ring 1 retains an annular inner member 2 of substantially triangular cross-section by means of securing means 5, such as pins, rivets, threaded fasteners, or the like. The inner member 2 has formed on an outer circumferential wall surface 2A and an end face surface 2B thereof angularly consecutive spaced-apart discrete segments or webs 4 having outermost surfaces which engage the inner cylindrical circumferential wall surface and the circular annular inside end face surface of the outer ring 1 and leave free between the same and the inner member 2 peripherally extending ducts or channels 3.

Ducts 3 communicate with one another via an annular passageway 3A which, in turn, communicates with a hollow hand grip 6 having an internal passageway 6A that is adapted for connection with an unillustrated vacuum source. Hence, proper positioning of the suction ring apparatus at the desired location on the eye, which will be described hereinbelow, and activation of the vacuum source causes the suction ring apparatus to become securely affixed to the eye, thereby providing stable support for a trepan when such is attached to the suction ring apparatus.

A surface 2C of the inner member 2 contacts the surface of the eye and is, in accordance with the radius of the eye, shaped slightly concave rather than rectilinear. For improved securing of the outer ring 1 to the eye, the contours of the bottom and top edges thereof are offset relative to those of the inner member 2. The presence of the inner member 2 with its uniquely sized and shaped eye-contacting surface 2C prevents deformation of the eyeball when the apparatus is under vacuum.

As FIG. 1 also shows, the hollow grip 6 may be releasably secured to the ring 1, such as, for example, by threaded connection 6B, so as to project substantially radially therefrom at an angle relative to the central axis A of the apparatus. The ring is positioned on the eye by means of the grip 6 which can be used to move the eye after the ring apparatus has been fixed thereto. The edge 8 of the outer ring 1 that defines the upper opening 7 of the ring is placed on the eye at the corneal limbus L, in a manner best seen with reference to FIG. 6. FIG. 1 further illustrates the provision of means for permitting attachment of a trepan to the outer ring 1, suct trepan most preferably being of the type disclosed in the aforenoted U.S. patent application Ser. No. 462,052, the disclosure of which is incorporated herein by reference in the illustrated embodiment these attachment means assume the form of dovetail guides, herein designated by the numeral 9. However, other suitable means for permitting attachment of a trepan to the suction ring apparatus may be used, if desired.

FIGS. 2-5 are included to provide the reader with a complete understanding of the structural nature of the inner annular member 2, particularly the discrete segments or webs 4 and the channels 3 formed therebetween.

Figure 6:
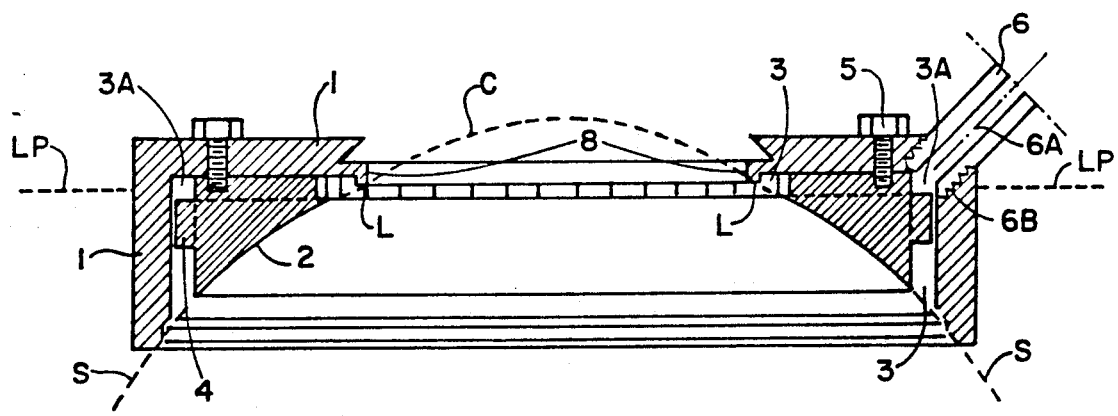
FIG. 6 is a view similar to FIG. 1 illustrating the proper positioning of the suction ring apparatus of the present invention on the corneal limbus of the human eye.

Turning to FIG. 6, along with the structural details of the suction ring apparatus illustrated and described hereinabove, there is also demonstrated the proper positioning of the suction ring apparatus of the present invention on a human eye, the features of which are outlined in phantom line. That figure clearly shows that the edge 8 defining the upper opening 7 of the outer ring 1 rests upon the corneal limbus L while the remainder of the eye-contacting structure of the suction ring apparatus contacts the sclera S. Hence, none of the suction ring apparatus contacts the cornea C.

Several benefits thus arise from the novel construction of the suction ring apparatus of the present invention and its ability to be positioned on the human eye in the manner depicted in FIG. 6. First, since the suction ring apparatus rests entirely on the corneal limbus L and the tough fibrous sclera S, the weight of the apparatus causes essentially negligible deformation of the eye. Second, due to the presence of the inner ring member 2 eye deformation is essentially prevented when the apparatus is under vacuum because eye wall expansion is contained by the eye-contacting surface 2C. Third, since the apparatus applies suction to the eye radially outwardly of the cornea C, i.e., at the sclera S, deformation of the eye is further prevented by avoiding the increase in the internal pressure of the eye which unavoidably results from the vacuum or suction ring devices of the prior art that apply suction directly to the cornea. Fourth, by the provision of the edge 8 which corresponds in diameter to and rests on the limbus L, the apparatus may be accurately and non-movably disposed exactly in the corneal limbus plane LP, thereby assuring that a trepan secured to the apparatus is guided perpendicularly to the limbus plane and concentrically with the optical axis.

While the present invention has been described in connection with the preferred embodiments of the various figures, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended claims.

We claim:

1. A suction ring apparatus for use in surgical operations on the human eye, said apparatus comprising:
   an annular outer ring having a circumferential wall and an end face and formed with a bore adapted for connection to a vacuum source;
   an annular inner ring member having a circumferential wall surface, an annular end face surface, and an eye-contacting surface; said inner ring member being provided on both the circumferential wall surface and the end face surface thereof with angularly spaced-apart means for engaging inner surfaces of the circumferential wall and the end face of said outer ring;
   said means for engaging defining channels between the circumferential wall surface and the annular end face surface of the inner ring member and the inner surfaces of the circumferential wall and end face of the outer ring, said channels communicating with one another and with said bore; and
   means for securing said inner member to said outer ring.

2. The apparatus of claim 1 wherein said securing means are releasable and extend through the outer ring end face.

3. The apparatus of claim 1 further comprising a hand grip attached to said outer ring and extending at an angle relative a central axis of the apparatus; said bore being coextensive with said hand grip.

4. The apparatus of claim 3 further comprising means for releasably attaching said hand grip to said outer ring.

5. The apparatus of claim 1 further comprising means for permitting attachment of a trepan to the outer ring.

6. The apparatus of claim 1 wherein the end face of the outer ring includes an edge defining a central opening in said end face, said edge corresponding in diameter to the diameter of the corneal limbus of a human eye and adapted for resting upon the corneal limbus when said suction ring apparatus is used in surgical operations on a human eye.

7. A suction apparatus for use in surgical trepanning operations on the human eye, said apparatus comprising:
   an outer annular ring having a circumferential wall and an end face, and an inner annular ring member retained within said outer annular ring, said outer annular ring including means for connecting said outer annular ring to a vacuum source, said inner annular ring member including means in communication with said means for connecting for permitting affixation of said outer annular ring to a human eye by vacuum;
   said end face of said outer annular ring including an edge defining a central opening wherein a trepan passes into contact with the cornea, said edge corresponding in diameter to the diameter of the corneal limbus of a human eye for resting only upon the corneal limbus outwardly of the cornea, means on said outer annular ring for carrying a trepan used in said surgical trepanning operations on the human eye while the outer annular ring and the inner annular ring do not contact the cornea and are immovably disposed in the plane of the cornea limbus when under vacuum, thereby enabling a guiding of a trepan perpendicular to the plane of the cornea limbus and within the optical axis.

* * * * *